(12) United States Patent
Miyamoto et al.

(10) Patent No.: US 7,631,544 B2
(45) Date of Patent: Dec. 15, 2009

(54) FLOW ANALYSIS SYSTEM

(75) Inventors: Masao Miyamoto, Okayama (JP);
Masayuki Suzuki, Okayama (JP)

(73) Assignee: Canon Semiconductor Equipment, Inc., Bando-shi, Ibaraki (JP)

( * ) Notice: Subject to any disclaimer, the term of this patent is extended or adjusted under 35 U.S.C. 154(b) by 249 days.

(21) Appl. No.: 11/661,903

(22) PCT Filed: Aug. 24, 2006

(86) PCT No.: PCT/JP2006/016593

§ 371 (c)(1),
(2), (4) Date: Mar. 2, 2007

(87) PCT Pub. No.: WO2007/023889

PCT Pub. Date: Mar. 1, 2007

(65) Prior Publication Data

US 2008/0060413 A1     Mar. 13, 2008

(30) Foreign Application Priority Data

Aug. 26, 2005  (JP) .............................. 2005-245843
Nov. 4, 2005   (JP) .............................. 2005-320530

(51) Int. Cl.
*G01N 29/00* (2006.01)
(52) U.S. Cl. .................................... 73/64.53
(58) Field of Classification Search ............... 73/64.53, 73/863.23, 61.59
See application file for complete search history.

(56) References Cited

U.S. PATENT DOCUMENTS 4,486,097 A * 12/1984 Riley ........................ 356/410
4,690,560 A * 9/1987 Coogan ...................... 356/338
4,798,803 A * 1/1989 Wolcott et al. .................. 436/52
5,935,625 A   8/1999 Hjok Nevik et al.

FOREIGN PATENT DOCUMENTS

| GB | 2126117 A | 8/1983 |
| JP | 59-060359 A | 3/1984 |
| JP | 08-178806 A | 12/1996 |
| JP | 08178806 | * 12/1996 |
| JP | 2003-344425 A | 3/2003 |
| JP | 2004-163191 A | 10/2004 |
| JP | 2004-321191 A | 11/2004 |
| WO | WO 96/35337 | 11/1996 |

OTHER PUBLICATIONS

International Preliminary Report on Patentability, 2008.

* cited by examiner

*Primary Examiner*—David A. Rogers
*Assistant Examiner*—Alex Devito
(74) *Attorney, Agent, or Firm*—Frishauf, Holtz, Goodman & Chick, P.C.

(57) ABSTRACT

A flow analysis flow analysis system having a deaerator for removing gas bubbles in a liquid upstream an analysis section. The deaerator comprises a liquid-containing means variable in internal volume for containing the liquid together with gas bubbles included in the liquid; a liquid-introducing means for introducing the liquid into the liquid-containing means; a gas bubble-discharging means for discharging gas bubbles in the liquid-containing means by decreasing the internal volume of the liquid-containing means while maintaining in the liquid-containing means at least part of the liquid introduced by the liquid-introducing means; and a liquid delivery means for delivering to the analysis section the liquid in the liquid-containing means from which gas bubbles have been discharged by the gas bubble-discharging means.

5 Claims, 13 Drawing Sheets

FLOW ANALYSIS SYSTEM

This application is a U.S. National Phase Application under 35 Usc 371 of International Application PCT/JP2006/316593, filed Aug. 24, 2006, which is incorporated herein in its entirety by this reference.

TECHNICAL FIELD

The present invention relates to techniques for deaerating liquids which contain gas bubbles in a flow analysis system (for example, flow injection analysis (FIA) system).

BACKGROUND ART

Flow analysis system (FIA, for example) is an analytical procedure capable of performing real-time, on-site analysis. In particular, such procedures are effective for on-site analyses for trace elements contained as impurities in chemicals in a process for fabricating semiconductors where such chemicals are used in extremely high purities. To briefly explain FIA here, it is a type of flow analysis in which a carrier (sample-carrying fluid) is flowed through a flow path, the carrier being substituted with an analytical sample at appropriate times, to react the analytical sample with a reaction reagent with which an element to be detected may develop colors so that the concentration of the element may be analyzed on the basis of the detection of the difference $\Delta$ in absorbance between the carrier and the analytical sample. More specifically, in FIA, a carrier and a reaction reagent are mixed and thoroughly stirred by means of agitation and dispersion before performing concentration detection (typically, measurement of absorbance on the basis of absorptiometry) using a detector for detecting element concentrations and, as such, by substituting the carrier with a sample at a time, the concentration of the sample is determined by measurement of the differential in absorbance. The disclosure of Japanese Unexamined Patent Publication (Kokai) No. 2004-163191 is to be incorporated herein by reference.

Patent Reference 1: Japanese Unexamined Patent Publication No. 2004-163191

Patent Reference 2: Japanese Patent Application No. 2004-321191

DISCLOSURE OF THE INVENTION

Problems to be Solved by the Invention

Incidentally, in processes for fabricating semiconductors, foamable liquid chemicals such as HPM and APM are used. As such, in analyzing such foamable liquid chemicals, when a sample is collected in a bottle or the like to perform a batch processing, foams may easily be removed even if the analyte is foamable. When FIA process is adopted, however, a liquid sample must be extracted from the stream and, if gas bubbles are included, the sample may not precisely be metered, causing an increase in error of the data. Further, in the case of measurement by absorptiometry, one of the most conventional methods, measurement is disabled when gas bubbles are included in a liquid analyte. Incidentally, the inventors have already proposed a strategy in which pretreatment liquid or treatment liquid is refrigerated against the foaming phenomenon due to exothermic reaction in pretreatment (Patent Reference 2). Currently, however, there are actually no countermeasures against the foaming phenomenon due to foamable liquid chemicals or against the gas bubbles inadvertently included in any of liquids involved in an analysis. Therefore, the present invention aims to provide a measure for enabling a stable analysis even when a liquid including gas bubbles that is involved in an analysis, such as a foamable liquid chemical exists, with no influences by such gas bubbles on the analysis.

Means for Solving the Problems

The present invention (1) is a flow analysis system having a deaerator (deaerator A) for removing gas bubbles in a liquid upstream of an analysis section, wherein the deaerator (deaerator A) comprises:

a liquid-containing means (space formed by sample syringe $A_3$ and plunger $A_{3-1}$) variable in internal volume for containing the liquid together with gas bubbles included in the liquid;

a liquid-introducing means (sample pump $A_2$ and pump control means Y) for introducing the liquid into the liquid-containing means (space formed by sample syringe $A_3$ and plunger $A_{3-1}$);

a gas bubble-discharging means (sample pump $A_2$ and pump control means Y) for discharging gas bubbles in the liquid-containing means by decreasing the internal volume of the liquid-containing means while maintaining in the liquid-containing means at least part of the liquid introduced by the liquid-introducing means (sample pump $A_2$ and pump control means Y); and a liquid delivery means (sample pump $A_2$ and pump control means Y) for delivering to the analysis section the liquid in the liquid-containing means (space formed by sample syringe $A_3$ and plunger $A_{3-1}$) from which gas bubbles have been discharged by the gas bubble-discharging means (sample pump $A_2$ and pump control means Y).

The present invention (2) is the flow analysis system according to the invention (1) further comprising a delivery amount control means (pump control means Y) for controlling the amount of liquid delivery, for controlling the liquid-introducing means (sample pump $A_2$ and pump control means Y) and the gas bubble-discharging means (sample pump $A_2$ and pump control means Y) in such a manner that the liquid introduction and the gas bubble discharge may be repeated until the liquid reaches a predetermined amount in the liquid-containing means (space formed by sample syringe $A_3$ and plunger $A_{3-1}$).

The present invention (3) is the flow analysis system according to the invention (1) or (2) wherein the liquid-containing means (space formed by sample syringe $A_3$ and plunger $A_{3-1}$) has an opening (sample inlet/outlet $A_{3-2}$) functioning as a gas bubble outlet, the opening being disposed in such a manner that gas bubbles may accumulate thereat when the gas bubbles are present in the liquid-containing means.

The present invention (4) is the flow analysis system according to the invention (3) wherein the liquid-containing means is composed of a syringe (sample syringe $A_3$) having the opening at its tip and a plunger (plunger $A_{3-1}$) inserted in the syringe and movable in the axial direction of the syringe, the plunger being installed generally in the vertical direction with the opening (sample inlet/outlet $A_{3-2}$) facing upward.

The present invention (5) is the flow analysis system according to the invention (3) or (4) wherein the opening (sample inlet/outlet $A_{3-2}$) functions as a liquid inlet for introducing the liquid into the liquid-containing means and/or as a liquid delivery port for delivering the liquid from the liquid-containing means to the analysis section and wherein the deaerator (deaerator A) further comprises a switching means (sample intake/discharge selector valve $A_5$) for switching in function between the gas bubble outlet and the liquid inlet and/or liquid delivery port.

The present invention (6) is the flow analysis system according to any one of the inventions (1) to (5) which is a flow injection analysis system.

Preferred embodiments are mentioned below.

A preferred embodiment (1) is a flow injection analysis system having a deaerator (deaerator A) for removing gas bubbles from a foamable liquid, wherein the deaerator (deaerator A) comprises:

a syringe-like container (sample syringe A) having an inlet (sample inlet/outlet $A_{3-2}$) for introducing the foamable liquid thereinto, a liquid outlet (sample inlet/outlet $A_{3-2}$) for discharging the foamable liquid to the outside, being the same one as or different from the inlet and a gas bubble outlet (sample inlet/outlet $A_{3-2}$) for discharging gas bubbles to the outside from the foamable liquid introduced, being the same one as or different from the inlet or the liquid outlet, the container being adapted to be variable in internal volume and disposed in such a manner that the gas bubbles from the foamable liquid may accumulate at the gas bubble outlet (sample inlet/outlet $A_{3-2}$) when the foamable liquid is contained therein;

a pump (sample pump $A_2$) for varying the internal volume of the syringe-like container (sample syringe $A_3$); and a pump control means (pump control means Y) for controlling the pump (sample pump $A_2$) for increasing the internal volume of the syringe-like container (sample syringe $A_3$) to introduce the foamable liquid into the syringe-like container (sample syringe $A_3$) and for decreasing the internal volume of the syringe-like container (sample syringe $A_3$) to discharge the gas bubbles accumulated at the gas bubble outlet (sample inlet/outlet $A_{3-2}$) from the syringe-like container (sample syringe $A_3$).

A preferred embodiment (2) is the flow injection analysis system according to the preferred embodiment (1) wherein the pump control means (pump control means Y) controls the pump (sample pump $A_2$) in such a manner that the introduction and discharge may be repeated until the foamable liquid reaches a predetermined amount in the syringe-like container (sample syringe $A_3$).

A preferred embodiment (3) is the flow injection analysis system according to the preferred embodiment (1) or (2) wherein the deaerator (deaerator A) further comprises a valve (sample intake/discharge selector valve $A_5$) for switching between a foamable liquid introduction flow path (sample intake pipe $A_1$) for introducing the foamable liquid into the syringe-like container (sample syringe $A_3$) and a foamable liquid delivery flow path (sample discharge pipe $A_4$) for delivering the foamable liquid in the syringe-like container (sample syringe $A_3$) out to a measurement section.

A preferred embodiment (4) is the flow injection analysis system according to the preferred embodiment (3) wherein the pump control means (pump control means Y) controls the pump (sample pump $A_2$) in such a manner the pump may discharge part of the foamable liquid contained in the syringe-like container (sample syringe $A_3$) together with the accumulated gas bubbles from the syringe-like container (sample syringe $A_3$) via the foamable liquid delivery flow path (sample discharge pipe $A_4$).

A preferred embodiment (5) is the flow injection analysis system according to the preferred embodiments (1) to (4) further comprising a second liquid delivery control means (pretreatment unit B, pump control means Y) for delivering a second liquid for treating the foamable liquid.

A preferred embodiment (6) is the flow injection analysis system according to the preferred embodiment (5) wherein the second liquid delivery control means (pretreatment unit B, pump control means Y) performs a first control for delivering the second liquid when treating the foamable liquid and a second control for delivering the second liquid into the flow path when removing gas bubbles in the flow path.

A preferred embodiment (7) is the flow injection analysis system according to any one of the preferred embodiments (1) to (6) wherein the container is syringe-like.

A preferred embodiment (8) is the flow injection analysis system according to any one of the preferred embodiments (1) to (7) wherein the inlet, the liquid outlet and the gas bubble outlet are one and the same port (sample inlet/outlet $A_{3-2}$).

Terms as used herein will now be defined with respect to their meanings. The term "liquid" refers to any liquid for which the presence of gas bubbles is of concern in, for example, an analysis, specific examples of which include liquid samples, liquid chemicals, liquid carriers and any combinations thereof. In addition, the terms "liquid" and "foamable liquid" refer to any liquid capable of generating gas bubbles, including not only that containing gas bubbles but also that containing ingredients per se foaming (vaporizing or decomposing, for example) to generate gases. The term "gas bubbles" means gas bubbles generated from a liquid, but not being bubble-like in a liquid-containing means. The term "system" is a concept which encompasses apparatuses. Detecting means for "analysis" are not particular limited and include an absorptiometer and ICP-MS, for example.

EFFECT OF THE INVENTION

According to the present invention, an advantageous effect is obtained that foamable samples such as HPM and SPM may be measured by FIA, because a liquid containing gas bubbles is introduced into a container and the gas bubbles are first discharged so that only the liquid remains in the container. Further, a stable analysis is enabled because a liquid analyte contains no gas bubbles while in an analysis section. In addition, various troubles caused by the existence of gas bubbles in lines may be avoided.

BEST MODE FOR CARRYING OUT THE INVENTION

The flow analysis system according to the best mode will be described below with reference to the drawings. In the best mode, a flow injection system is given as an example among flow analysis systems. Also in the best mode, an analysis for metal elements contained in a foamable liquid chemical to be used in a process for fabricating semiconductors is given as an example. First, FIG. 1 is a schematic drawing of a whole flow injection analysis system according to the best mode.

Figure 13:
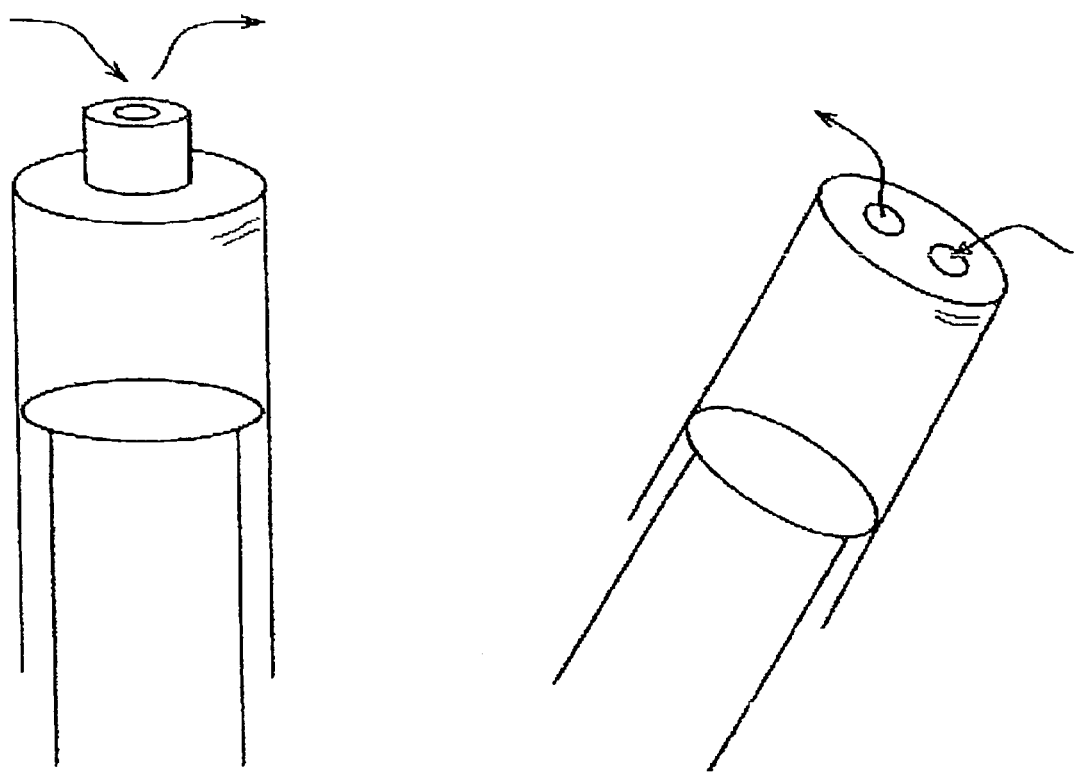
FIG. 13 is a drawing illustrating appearances of a syringe-like container, in which an aspect having an inlet/outlet is shown to the left and an aspect having an inlet and an outlet is shown to the right.

Features of the invention, namely, a deaerator A and a pretreatment unit B drivable in synchronization with the deaerator A are to be subsequently referred to. Though the best mode has an installed pretreatment unit B, installation of the pretreatment unit B is optional and it is needless to say that other modes with no pretreatment unit B will belong to the technical range of the present invention as along as they suffice other constituent features. Moreover, in the best mode, as shown to the left in FIG. 13, a syringe-like container has one opening which functions both as an inlet and as an outlet, but it may instead has an inlet and an outlet separately as shown to the right in FIG. 13. Further, though not shown, an inlet, a liquid outlet and a gas bubble outlet may each be provided as a separate opening.

Figure 1:
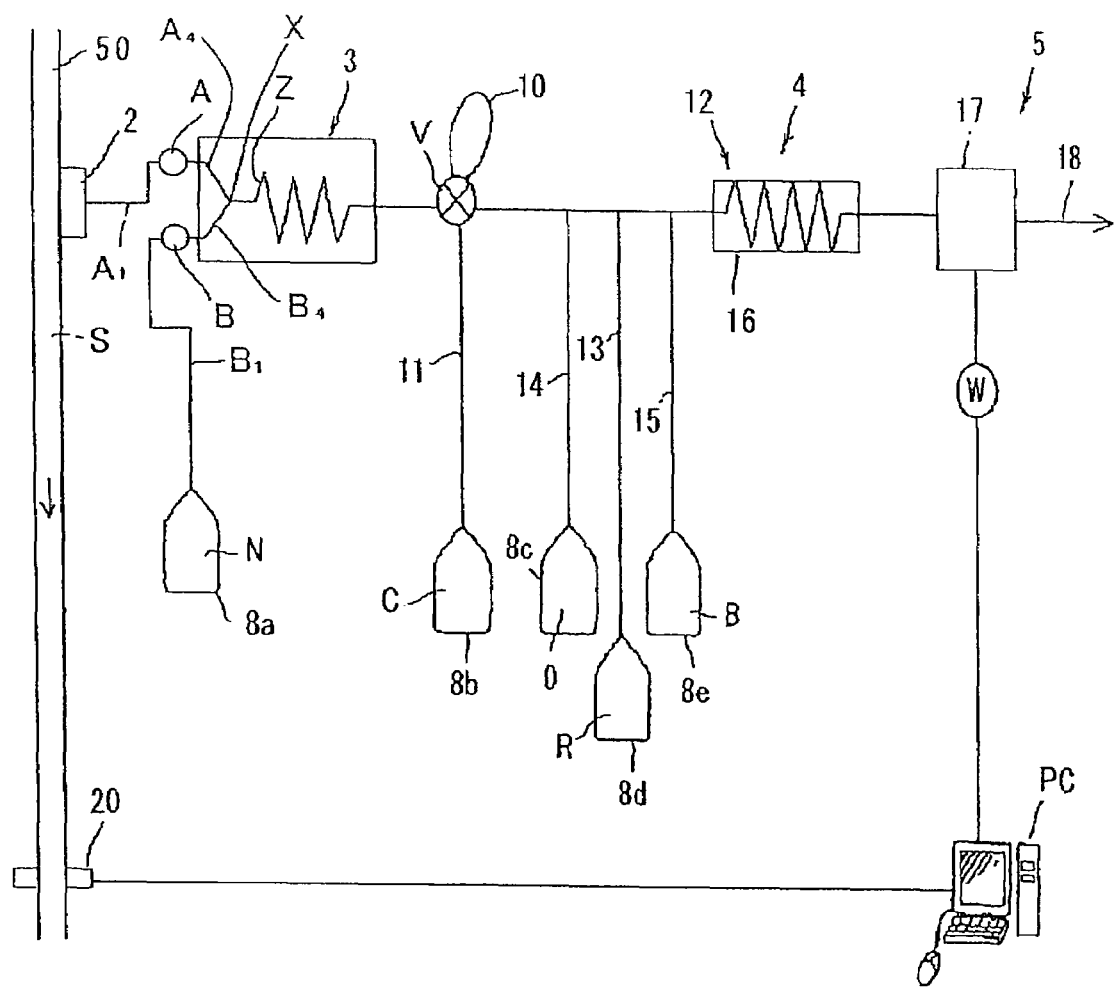
FIG. 1 is a schematic drawing of an FIA system according to the best mode.

Described now with reference to FIG. 1, the system includes, at least, a sampling means 2 for obtaining a sample S at a fixed time interval from a predetermined chemicals line in a process for fabricating semiconductors, a pretreatment means 3 for mixing the sample S with a pretreatment liquid N to pretreat the sample S, a reaction means 4 for mixing a coloring reagent R for producing colors by undergoing an oxidative reaction catalyzed by a metal ion, an oxidizing agent O and a buffer solution B at a predetermined ratio to cause a color developing reaction and an absorptiometric means 5 for determining the absorbance of the sample S which has undergone a color developing reaction by the reaction means 4. Each element will be described in detail below.

First, the sampling means 2 is installed along a chemicals flow pipe 50 through which a liquid chemical to be used in a process for fabricating semiconductors flows. A fixed amount of sample S is obtained at a fixed time interval from the chemicals flow pipe 50.

Next, the deaerator A is in fluid communication with a sample intake pipe $A_1$. Obtained by the sampling means 2, the sample S will then be subjected to a deaeration treatment by the deaerator A, before being led to a pretreatment pipe Z downstream (more specifically, at confluence X with a second liquid discharge pipe $B_4$).

On the other hand, the pretreatment liquid N is encapsulated in a chemicals bag 8a and the chemicals pack 8a is connected with a second liquid intake pipe $B_1$. The second liquid intake pipe $B_1$ is in fluid communication with a pretreatment unit B to be subsequently referred to. The pretreatment liquid N from the chemicals bag 8a is led via the pretreatment unit B to the pretreatment pipe Z downstream (more specifically, at confluence X with a second liquid discharge pipe $B_4$). Reagents used in the present system, including the pretreatment liquid N, are all contained in chemicals bags to minimize inclusion of impurities from outside the system.

The sample S and the pretreatment liquid N flowed into the pretreatment pipe Z of the treatment means 3 are then mixed while flowing through the pretreatment pipe Z so that the sample S may be treated. In so doing, flow rates of the sample and the pretreatment liquid N flowed into the pretreatment pipe Z will automatically be controlled as subsequently described.

The pretreatment pipe Z is connected to an automatic selector valve V. The automatic selector valve V is provided with a sample metering pipe 10 which is capable of holding a fixed amount of sample.

Connected to the selector valve V is a carrier flow pipe 11. Connected to the carrier flow pipe 11 at its end is a reagent bag 8b for encapsulating a carrier C.

The automatic selector valve V is switched at an appropriate timing while the carrier C is allowed to flow into the carrier flow pipe 11, so that the carrier may flow into the sample holding pipe 10. As a result, the sample held in the sample holding pipe 10 is pressed by the carrier C to flow into a reaction pipe 12 of the reaction means 4.

Upstream the reaction means 4, a coloring reagent flow pipe 13 which is connected to a reagent bag 8c in which a coloring reagent R (a reagent developing colors by undergoing an oxidative reaction catalyzed by a metal ion) is encapsulated, an oxidizing agent flow pipe 14 which is connected to a reagent bag 8d in which an oxidizing agent O is encapsulated and a buffer solution flow pipe 15 which is connected to a reagent bag 8e in which a buffer solution B is encapsulated are connected to the reaction pipe 12.

The reaction pipe 4 mixes each of the coloring reagent R, the oxidizing agent O and the buffer solution B to be used as necessary with the sample S or the carrier C to promote oxidizing reactions. In a flow injection analysis system, reaction times may be controlled by adjusting the length of the reaction pipe 12. It is also possible to adjust reaction temperatures by providing the reaction pipe 12 (especially its downstream side) within a temperature regulator 16.

In addition, each flow pipe is provided with a mechanism for adjusting the flow rate of a reagent (not shown). Therefore, conditions that are most preferable for a coloring reagent to develop colors may easily be created by adjusting the flow rate of each flow pipe on the basis of pH, concentration and the like of a solution flowing in each flow pipe.

The reaction pipe 12 is connected to an absorptiometer 17 as an absorptiometric means. The absorptiometer 17 measures the absorbance of the sample S or the carrier C. The sample S whose absorbance has been measured is discharged through a discharge pipe 18. Based on the difference Δ in absorbance between the both, the concentration of an analyte in the liquid sample S is then determined.

Figure 2:
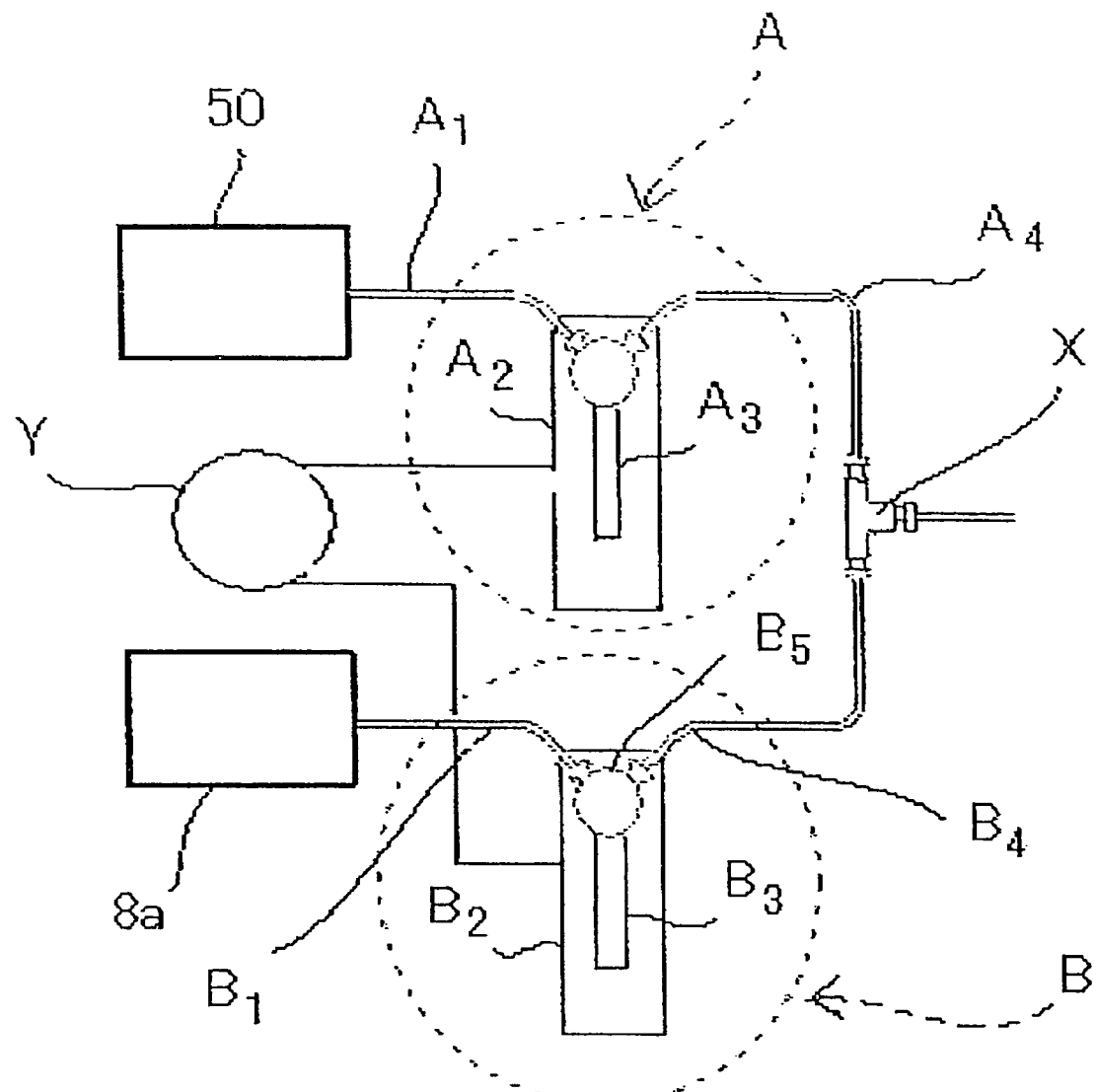
FIG. 2 is a schematic drawing of a deaerator and pretreatment unit according to the best mode.
Figure 7:
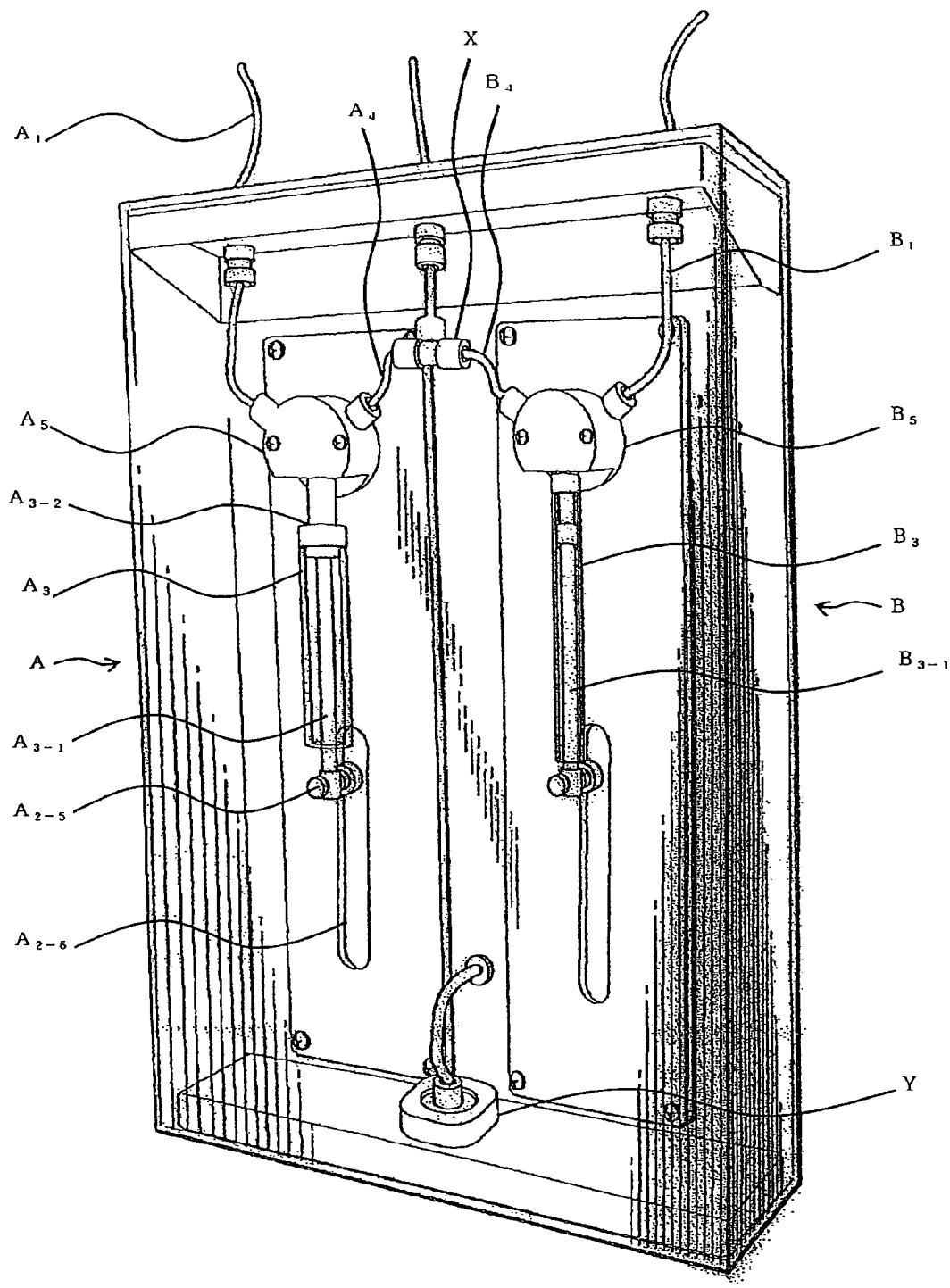
FIG. 7 is a front view of the deaerator and pretreatment unit according to the best-mode.
Figure 8:
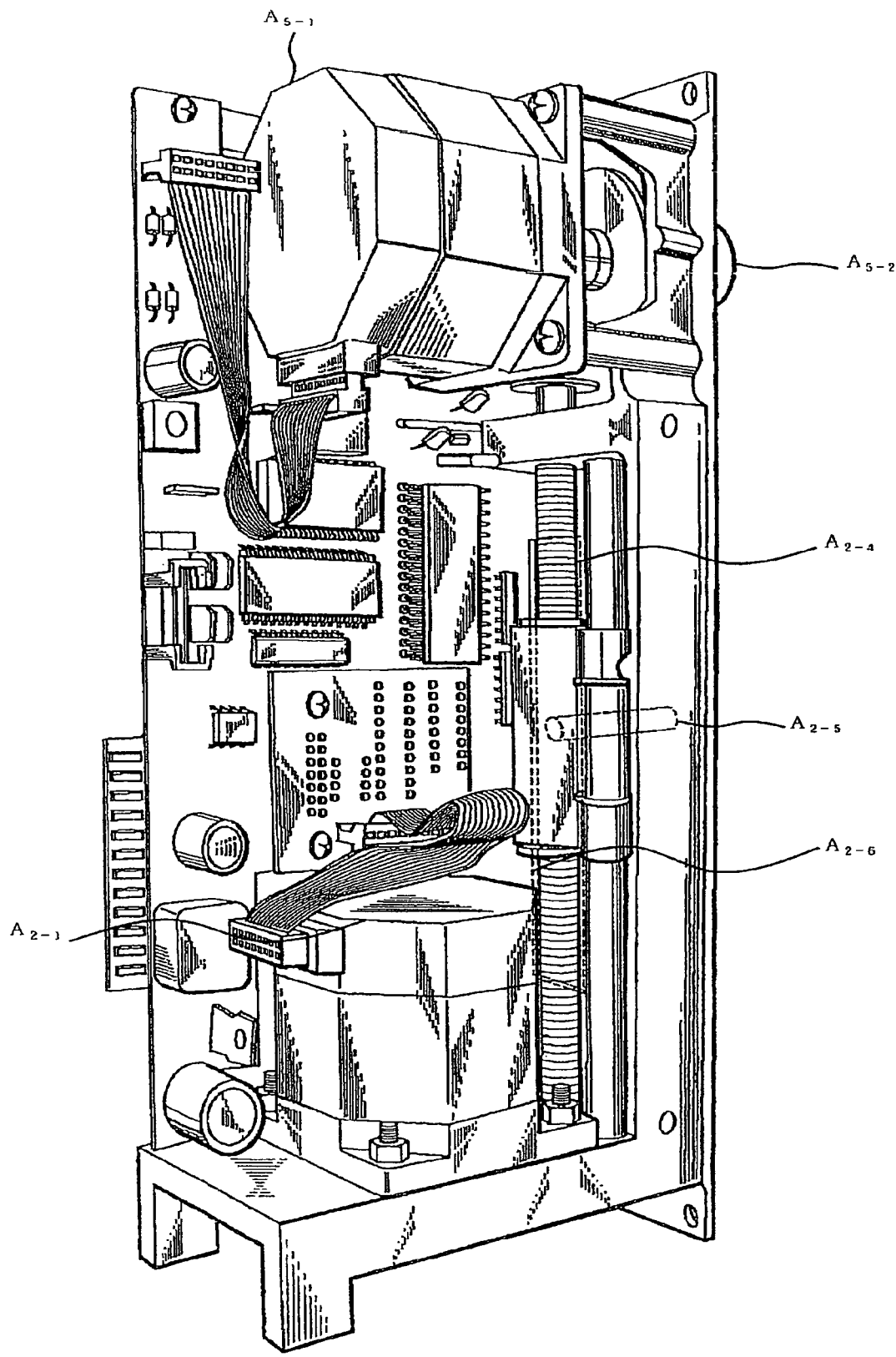
FIG. 8 is a back side perspective view of the deaerator and pretreatment unit according to the best mode (as disassembled)
Figure 9:
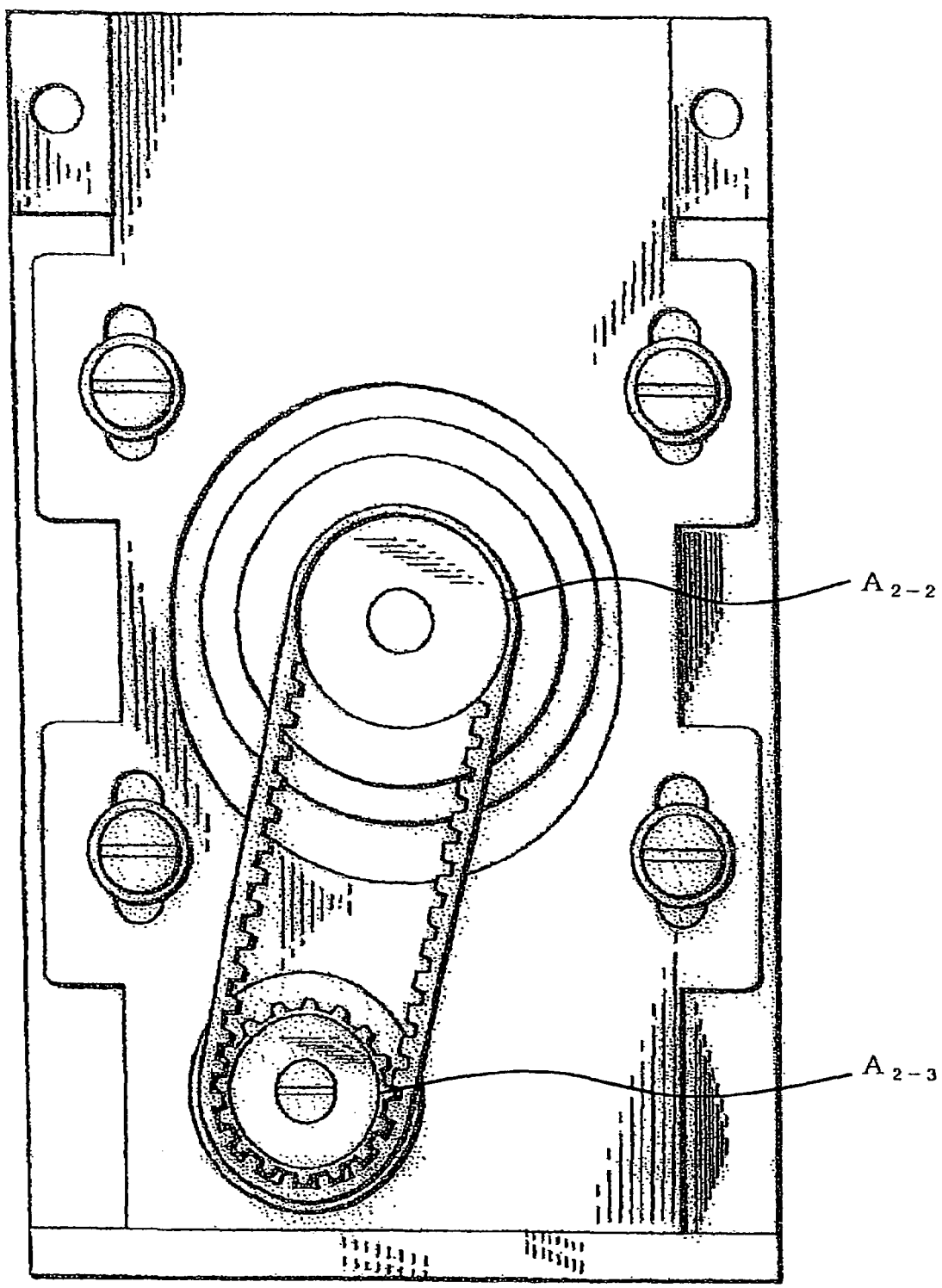
FIG. 9 is a bottom view of the deaerator and pretreatment unit according to the best mode.

With reference to FIG. 2, the deaerator A and the pretreatment unit B according to the best mode will be described next. As seen from FIG. 2, the deaerator A and the pretreatment unit B are connected with a pump control means Y and operate under the control of the means Y as subsequently described. Among these elements, the deaerator A is first described in detail. The deaerator A is composed of a sample intake pipe $A_1$, a sample pump $A_2$, a sample syringe $A_3$, a sample discharge pipe $A_4$ and a sample intake/discharge selector valve $A_5$. Each element will be described in detail below with reference to FIG. 7 to FIG. 9 illustrating details of the deaerator A and the pretreatment unit B.

First, the sample intake pipe $A_1$ is a pipe for guiding the sample to the sample syringe $A_3$ when sucking the sample.

When the sample intake pipe $A_1$ has a larger inner diameter, the pressure exerted on the sample by suction will diminish so that intake of gas bubbles when sucking them may be suppressed, whereas when it has a large diameter, its volume will increase so that it may take more time to exchange liquids in the sample intake pipe $A_1$. As such, the volume of the sample intake pipe $A_1$ is preferably 1.6 times or less the volume of the sample syringe $A_3$. For instance, when the volume of the sample syringe $A_3$ is 1 ml, the pipe may have an inner diameter of 1 mm and a length of 2 m.

Next, the sample pump $A_2$ can function as a power unit for effecting intake and discharge of the sample into and out of the sample syringe $A_3$ and vary the inner volume of the sample syringe $A_3$ and the velocity of a plunger. Specifically, introduction of the sample is effected by driving the plunger downward, while discharge of the sample is effected by driving the plunger upward. Schematic configuration of the sample pump $A_2$ is shown in FIG. 8 and FIG. 9. As shown, the sample pump $A_2$ is composed of a motor $A_{2-1}$, a first flange $A_{2-2}$ connected with the motor $A_{2-1}$, a second flange $A_{2-3}$ to which rotational drive of the first flange $A_{2-2}$ is transmitted via a belt, a threaded shaft $A_{2-4}$ to which rotational drive of the second flange $A_{2-3}$ is transmitted, a plunger joint $A_{2-5}$ movable by rotation of the shaft $A_{2-4}$, and a slit $A_{2-6}$ regulating vertical movement of the plunger joint $A_{2-5}$.

Next, for a sample and gas bubbles to be allowed to enter, the sample syringe $A_3$ should preferably be free from contamination on its surface to be in contact with a liquid and tend to let down gas bubbles. Specifically, glass and Teflon® materials are preferable. In addition, the sample syringe $A_3$ must be positioned in such a manner that gas bubbles may accumulate at the sample inlet/outlet $A_{3-2}$ so that the gas bubbles in a liquid sample may separate from the liquid and the gas bubbles may easily be removed when the liquid sample is introduced into the sample syringe $A_3$.

Preferably, as shown in FIG. 7, the sample inlet/outlet $A_{3-2}$ is installed at the upper section of the sample syringe $A_3$. In this case, the cross sectional area of the container is preferable larger since the gas bubbles tend to collect in the upper section of the sample syringe $A_3$. Specifically, a cylindrical sample syringe should preferably have an inner diameter of at least 4.5 mm.

Next, the sample discharge pipe $A_4$ should preferably have a less volume in consideration of that a sample taken in into the sample syringe $A_3$ is used to remove gas bubbles from the sample discharge pipe $A_4$. It should preferably have a volume of 60 µl or less, for example, an inner diameter of 0.5 mm with a length of 30 cm or less. In addition, materials and inner shapes of the sample discharge pipe $A_4$ should preferably be free from contamination and tend to let down gas bubbles. For example, Teflon® or glass materials with no roughness on the inner surface are preferable.

The sample intake/discharge selector valve $A_5$ should preferably be automatically switchable in intake and discharge of the sample and be free of contamination. Schematic configuration of the sample intake/discharge selector valve $A_5$ is shown in FIG. 7 and FIG. 8. As shown, the sample intake/discharge selector valve $A_5$ has a motor $A_{5-1}$ and a switch shaft $A_{5-2}$ which varies the rotational angle (intake side or discharge side) by being driven by the motor $A_{5-1}$. When the sample intake/discharge selector valve $A_5$ is switched to the intake side, the sample intake pipe $A_1$ is in fluid communication with the sample syringe $A_3$. Driving the plunger $A_{3-1}$ of the sample pump $A_2$ downward in this condition will allow the sample and the gas bubbles to pass through the sample intake pipe $A_1$ to be introduced into the sample syringe $A_3$. On the other hand, when the sample intake/discharge selector valve $A_5$ is switched to the discharge side, the sample discharge pipe $A_4$ is in fluid communication with the sample syringe $A_3$. Driving the plunger $A_{3-1}$ of the sample pump $A_2$ upward in this condition will allow the sample and the gas bubbles in the sample syringe $A_3$ to be discharged into the sample discharge pipe $A_4$.

The pretreatment unit B will be described next. The unit B is composed of a second liquid intake pipe $B_1$, a second liquid pump $B_2$, a second liquid syringe $B_3$, a second liquid discharge pipe $B_4$ and a second intake/discharge selector valve $B_5$. Fundamental configuration of the unit B is basically identical to that of the unit A.

First, the second liquid intake pipe $B_1$ is a pipe for guiding a second liquid to the second liquid syringe $B_3$ when sucking the second liquid. The second liquid intake pipe $B_1$ should preferably be made of an uncontaminated material including, but not particularly limited to, Teflon®. The second liquid pump $B_2$ is a power unit for effecting intake into and discharge from the second liquid syringe $B_3$ and is not particular limited with respect to its operation. The second liquid syringe $B_3$ is not particular limited as long as it is made of an uncontaminated material. The second liquid discharge pipe $B_4$ is a pipe into which the second liquid in the second liquid syringe $B_3$ is discharged and is not particular limited with respect to specification and the like as long as it is free of contamination. The second liquid intake/discharge selector valve $B_5$ should preferably be automatically switchable in intake and discharge of the second liquid and be free of contamination. When the second liquid intake/discharge selector valve $B_5$ is switched to the intake side, the second liquid intake pipe $B_1$ is in fluid communication with the second liquid syringe $B_3$. Driving the plunger $B_{3-1}$ of the second liquid pump $B_2$ downward in this condition will allow the second liquid to pass through the second liquid pipe $B_1$ to be introduced into the second liquid syringe $B_3$. On the other hand, when the second liquid intake/discharge selector valve $B_5$ is switched to the discharge side, the second liquid discharge pipe $B_4$ is in fluid communication with the second liquid syringe $B_3$. Driving the plunger $B_{3-1}$ of the second liquid pump $B_2$ upward in this condition will allow the second liquid in the second liquid syringe $B_3$ to be discharged into the second liquid discharge pipe $B_4$.

As shown in FIG. 7, in the best mode, the deaerator A is integral with the pretreatment unit B. The bottom surface has a leak sensor Q installed for detecting leak of liquids.

Next, with reference to FIG. 3 to FIG. 6, driving of pumps of the deaerator A and the pretreatment unit B by the drive control means Y is described in time sequence using dilution of a foamable sample with ultrapure water as an example.

Figure 3:
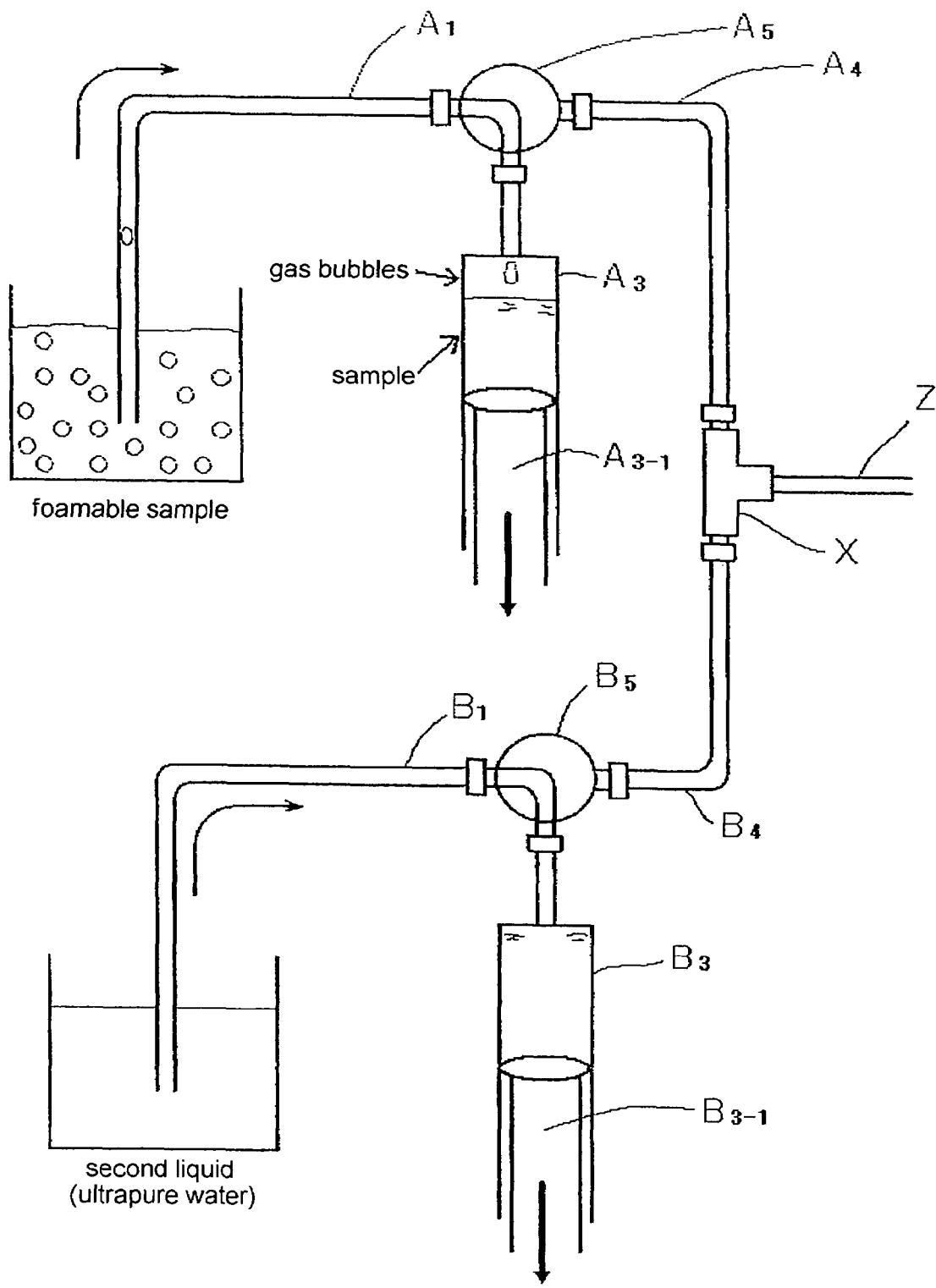
FIG. 3 is a drawing representing the operation of the deaerator and pretreatment unit according to the best mode (first phase)

FIG. 3 illustrates sampling of the sample and the second liquid. Specifically described, the sample intake/discharge selector valve $A_5$ is switched to the intake side to connect the sample intake pipe A with the sample syringe $A_3$. Driving the plunger $A_{3-1}$ downward by the sample pump $A_2$ will allow the sample and the gas bubbles to pass through the sample intake pipe $A_1$ to be introduced into the sample syringe $A_3$. If the intake rate is slower, then intake of the gas bubbles will be more suppressed. In addition, when the sample intake pipe $A_1$ has a larger inner diameter, the pressure exerted by suction on the sample will diminish so that intake of gas bubbles when sucking them may be suppressed. To give a specific example, when the sample intake pipe $A_1$ has an inner diameter of 1 mm, an intake rate of 2.5 ml/min or less is preferable. After intake of the sample and the gas bubbles, the liquid sample and the gas bubbles have accumulated in the lower and upper sections respectively in the sample syringe $A_3$ as shown in FIG. 3. Next, the second liquid intake/discharge selector valve $B_5$ is switched to the intake side to connect the second liquid intake pipe $B_1$ with the second liquid syringe $B_3$. Driving the plunger $B_{3-1}$ downward by the second liquid pump $B_2$ will then allow the second liquid to pass through the second liquid intake pipe $B_1$ to be introduced into the second liquid syringe $B_3$.

Figure 4:
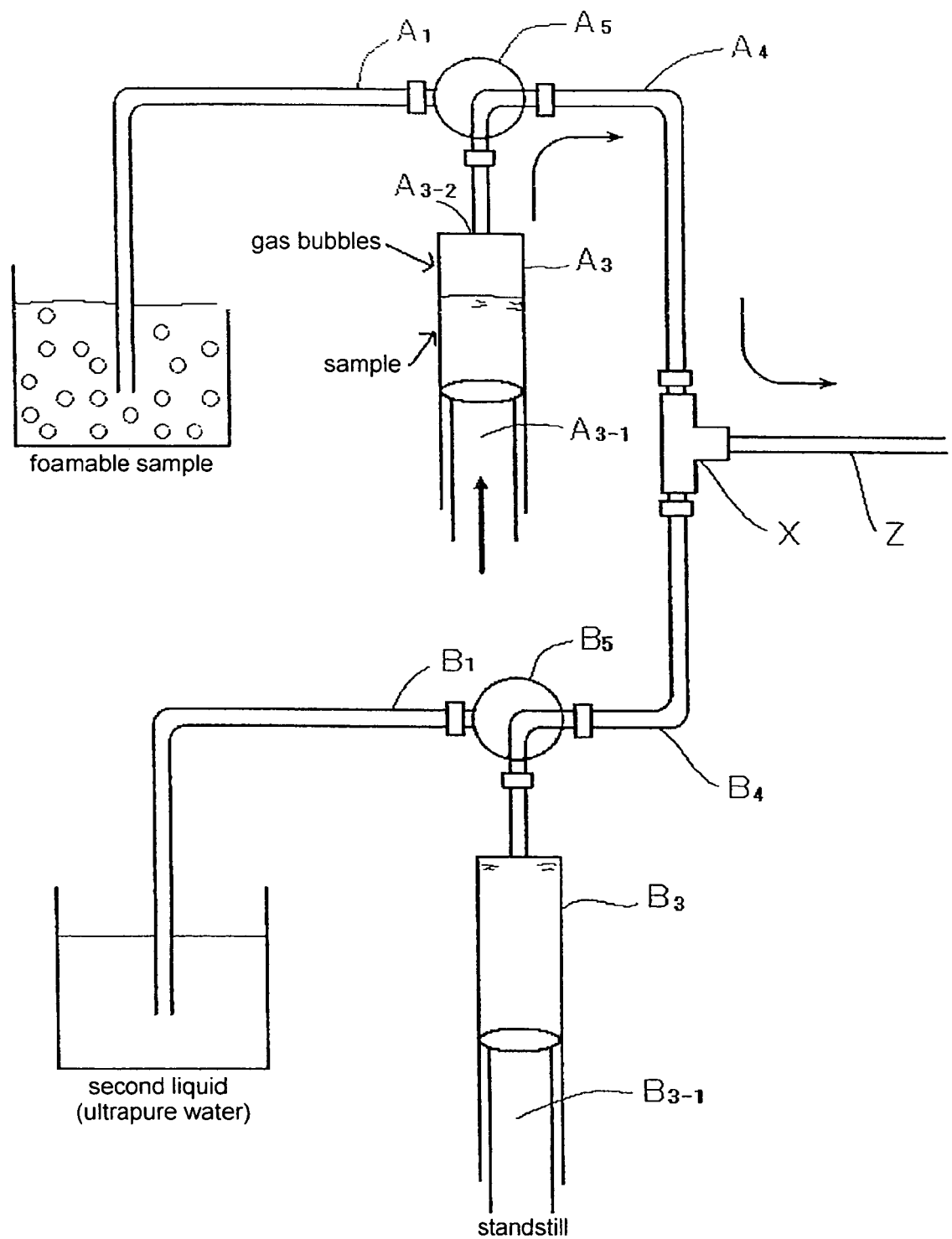
FIG. 4 is a drawing representing the operation of the deaerator and pretreatment unit according to the best mode (second phase)

Next, FIG. 4 illustrates discharge of gas bubbles from the sample syringe $A_3$ and the sample discharge pipe $A_4$. Specifically described, the sample intake/discharge selector valve $A_5$ is switched to the discharge side to connect the sample discharge pipe $A_4$ with the sample syringe $A_3$. Driving the plunger $A_{3-1}$ upward to a predetermined position by the sample pump $A_2$ will allow the gas bubbles accumulated at an upper inlet $A_{3-2}$ of the sample syringe $A_3$ to be discharged into the sample discharge pipe $A_4$. Also, driving the plunger $A_{3-1}$ upward to a predetermined position by the sample pump $A_2$ will allow a predetermined amount of sample in the sample syringe $A_3$ to be discharged into the sample discharge pipe $A_4$, thereby discharging the gas bubbles in the sample discharge pipe $A_4$ into a treatment liquid flow pipe Z.

Figure 5:
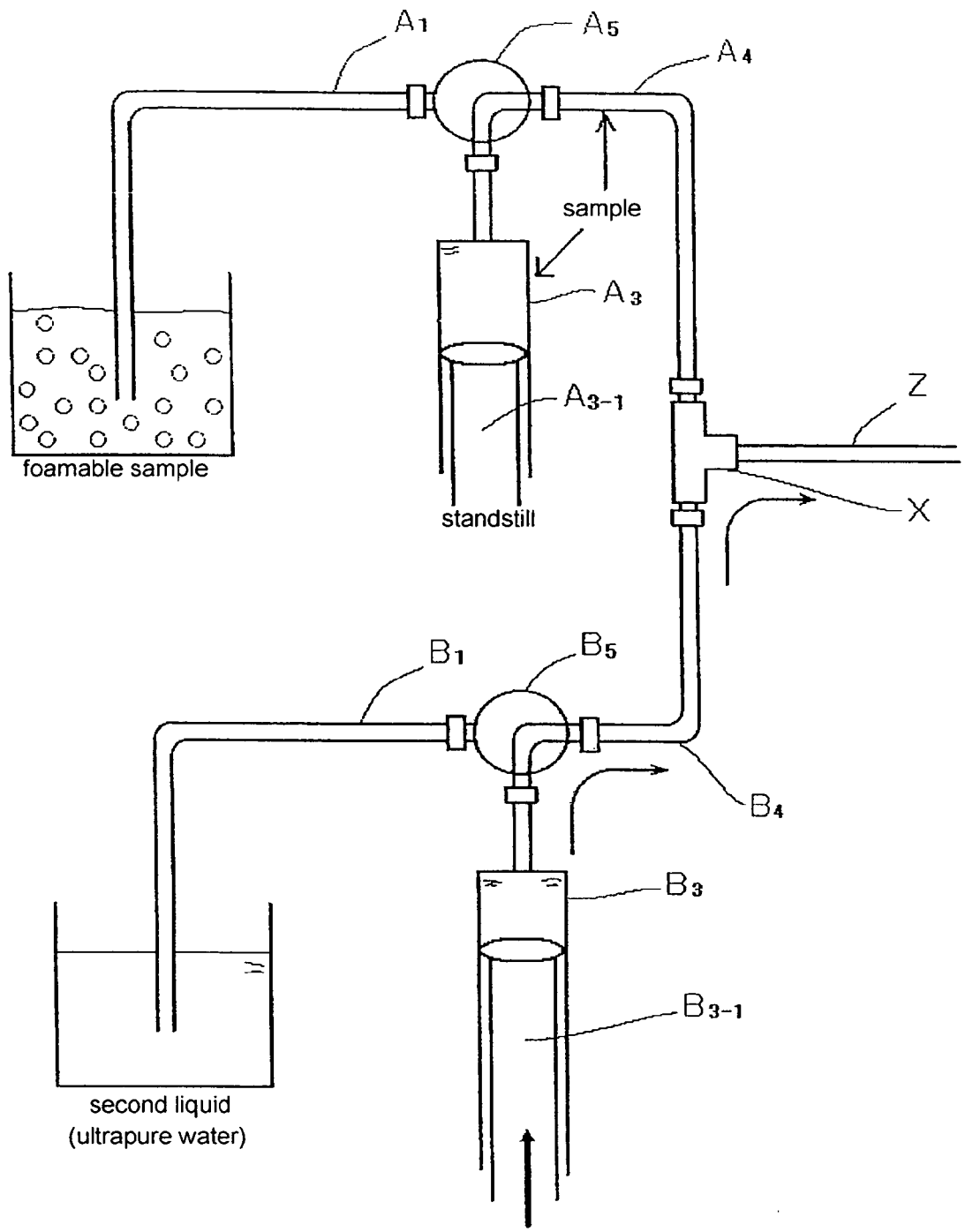
FIG. 5 is a drawing representing the operation of the deaerator and pretreatment unit according to the best mode (third phase)

Next, FIG. 5 illustrates discharge of the gas bubbles in the treatment liquid flow pipe Z by discharge of the second liquid from the second liquid syringe $B_3$. Specifically described, the second liquid intake/discharge selector valve $B_5$ is switched to the discharge side to connect the second liquid discharge pipe $B_4$ with the second liquid syringe $B_3$. Driving the plunger $B_{3-1}$ upward by the second liquid pump $B_2$ will allow the second liquid in the second liquid syringe $B_3$ to be discharged into the second liquid discharge pipe $B_4$ to be introduced into the treatment liquid flow pipe Z. The gas bubbles in the treatment liquid flow pipe Z will be discharged by the second liquid from the treatment liquid flow pipe Z.

Figure 6:
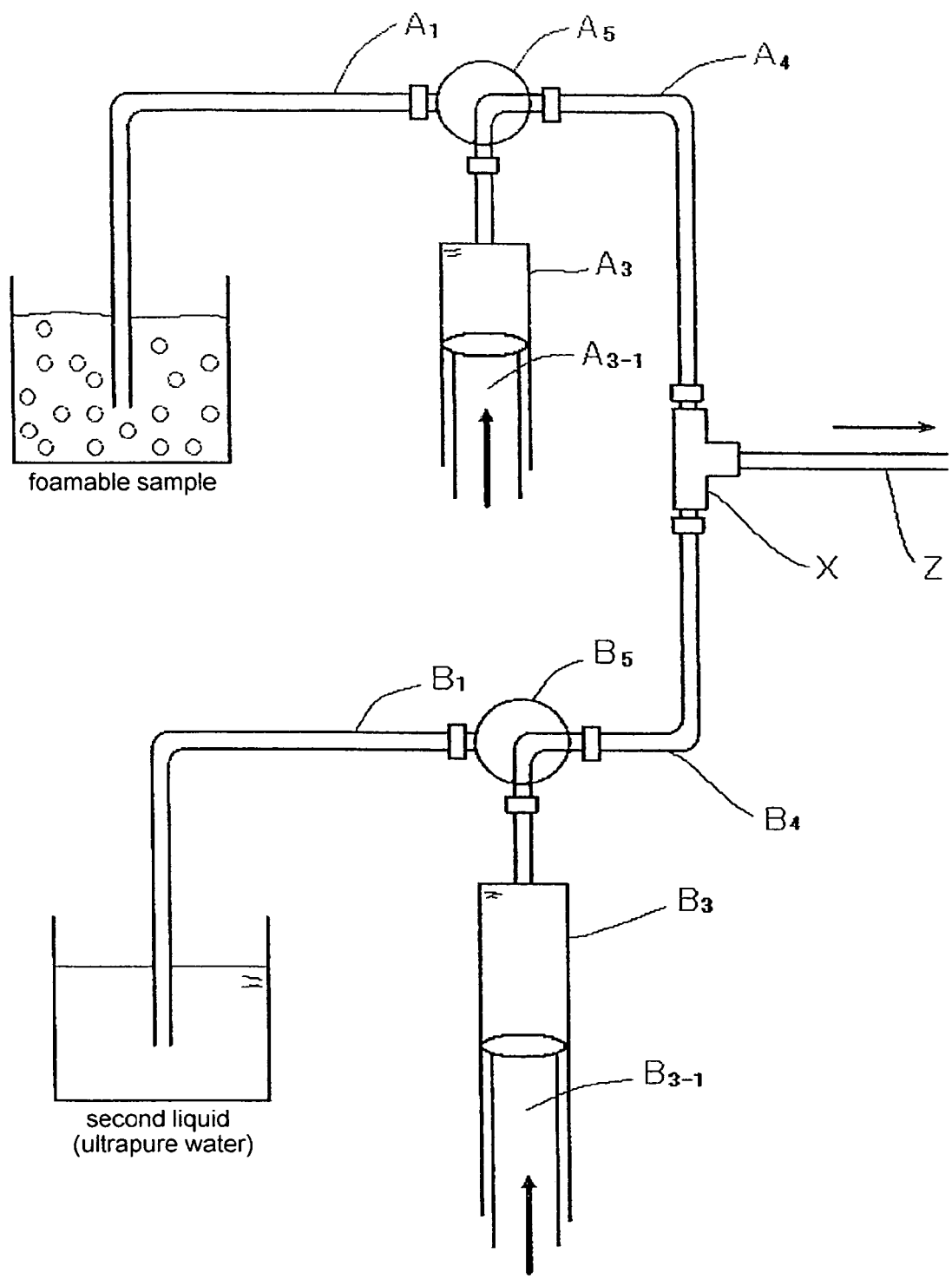
FIG. 6 is a drawing representing the operation of the deaerator and pretreatment unit according to the best mode (fourth phase)

Finally, FIG. 6 illustrates dilution of a foamable sample with the second liquid. Specifically described, the second liquid intake/discharge selector valve $B_5$ is switched again to the intake side to connect the second liquid intake pipe $B_1$ with the second liquid syringe $B_3$. Driving the plunger $B_{3-1}$ downward by the second liquid pump $B_2$ will allow the second liquid to pass through the second liquid intake pipe $B_1$ to be introduced into the second liquid syringe $B_3$. Then, the sample intake/discharge selector valve $A_5$ is switched to the discharge side to connect the sample discharge pipe $A_4$ with the sample syringe $A_3$. Also, the second liquid intake/discharge selector valve $B_5$ is switched to the discharge side to connect the second liquid discharge pipe $B_4$ with the second liquid syringe $B_3$. Thereafter, synchronous operation of the sample pump $A_2$ and the second liquid pump $B_2$ will drive the plungers $A_{3-1}$ and $B_{3-1}$ upward. In this way, the sample will be discharged into the sample discharge pipe $A_4$ and the second liquid will be discharged into the second liquid discharge pipe $B_4$, with a result that the sample may be diluted and mixed in a mixer pipe X.

A procedure for deaerating operation in the system according to the best mode will be described next. An operator will input empirically derived control information via an input means not shown, in consideration of the type of foamable samples, temperatures and the like. Receiving such input information, the drive control means Y will automatically drive the pumps of the deaerator A and the pretreatment unit B and provide control for automatic valve switching.

EXAMPLES

Experiment 1

Confirmation of Effect of Gas Bubbles on FIA Measurement

Using the FIA system shown in FIG. 1, an experiment for confirming the effect of gas bubbles on FIA measurement was carried out. In this experiment, however, a sample was not obtained from the chemicals flow pipe 50 but from a container containing the sample. Also, in this experiment, no pretreatment liquid N was used. Conditions for measurement are shown in Table 1. In this experiment, a liquid sample to which gas bubbles were artfully included when injecting the sample into a metering pipe was designated "undeaerated" and the opposite was designated "deaerated." Also in the table, "DPD" stands for N,N-dimethyl-p-phenylenediamine.

TABLE 1

| | formulation of liquid chemical | flow velocity (μl/min) | liquid delivery time (min) |
|---|---|---|---|
| B | 3M ammonium acetate | 500 | 3 |
| R | 0.16% DPD 0.2 mM citric acid | 100 | 3 |
| O | 10% hydrogen peroxide solution | 100 | 3 |
| C | 0.01M HCl | 500 | 6 |
| S | 0.01M HCl (blank) | — | — |

Figure 10:
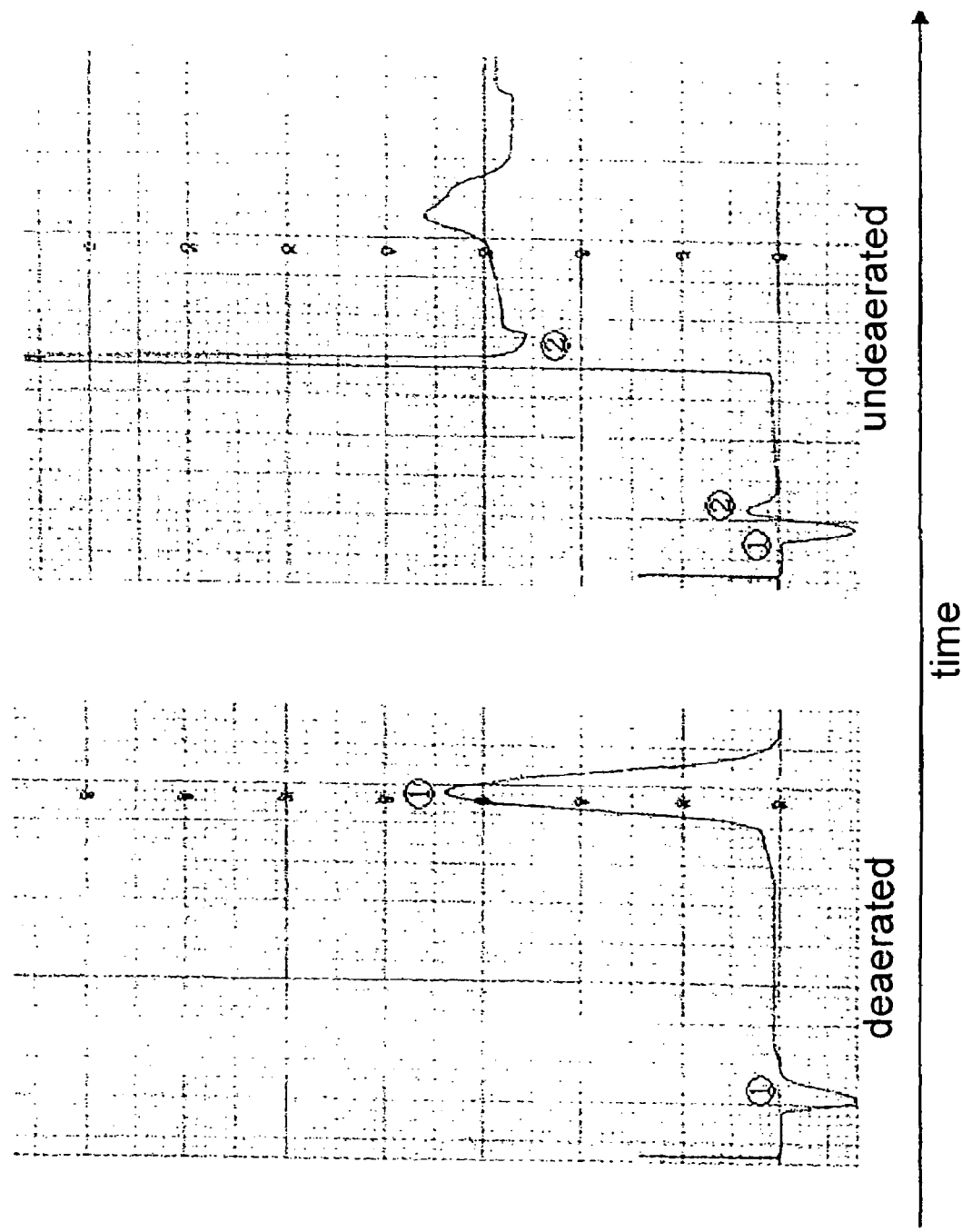
FIG. 10 is a chart representing the results of Experiment 1 of Examples.

The results are shown in FIG. 10. Shown to the left is "deaerated" and shown to the right is "undeaerated" in FIG. 10. In the drawing, "1" shows variation in absorbance due to variation in refractive index due to difference in concentrations of liquid chemicals and "2" shows variation in absorbance due to gas bubbles. As seen apparent from this drawing, the baseline fluctuates for "undeaerated."

Experiment 2

Measurement of deaerated Samples by FIA Under Respective Sample Conditions

FIA System

The FIA system shown in FIG. 1 was used for this experiment. In this experiment, however, a sample was not obtained from the chemicals flow pipe 50 but from a container containing the sample. Also, the deaerator A and the pretreatment unit were controlled by a PC. Specifications of the deaerator A and the pretreatment unit are as follows.

Deaerator A (Liquid Sample)

Syringe pump $A_2$: XL-3000 by TECAN, high resolution with 24,000 steps

Syringe $A_3$: body/Pyrex® glass (i. d. 4.5 mm, volume 1 ml); piston material/Teflon®; piston rod/stainless steel Pretreatment Unit B (diluent)

Syringe pump $B_2$: XL-3000 by TECAN, high resolution with 24,000 steps

Syringe $B_3$: body/Pyrex® glass (i. d. 14.5 mm, volume 10 ml); piston material/Teflon®; piston rod/stainless steel Flow pipe from deaerator to confluence X PTFE tube by Chukoh Chemical Industries, Ltd., i. d. 0.5 mm×30 cm (60 μl)

Flow pipe Z from confluence X onward

PTFE tube by Chukoh Chemical Industries, Ltd., i. d. 0.5 mm×30 cm (60 μl)

Figure 11:
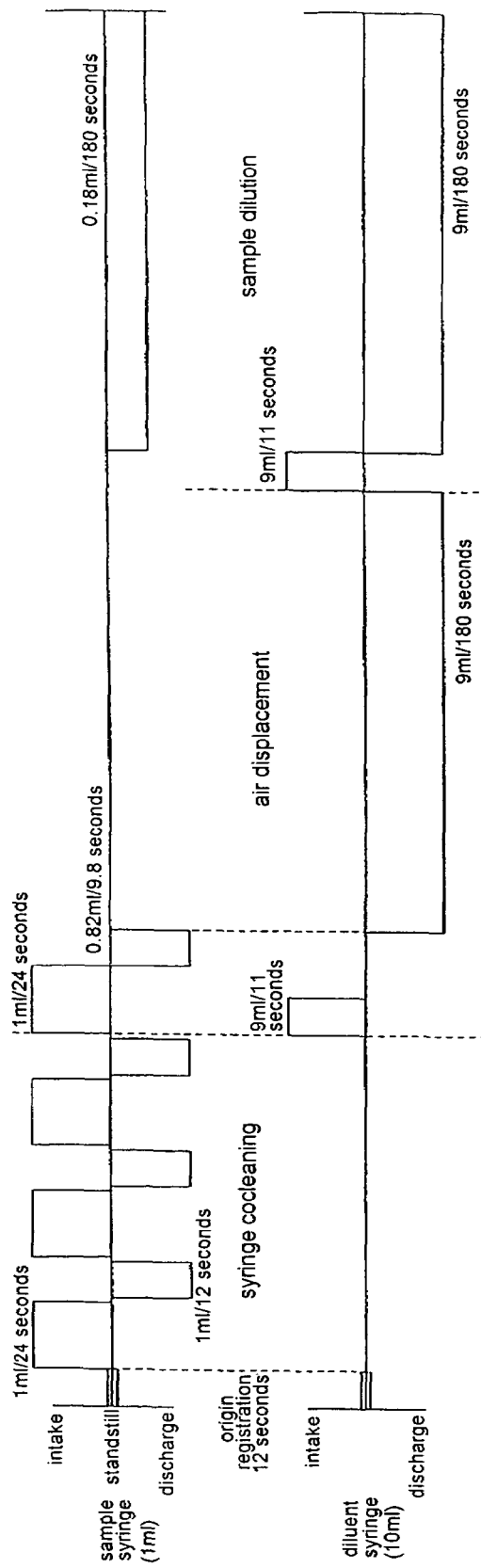
FIG. 11 is a timing chart representing the time-series operation of the deaerator and pretreatment unit of Experiment 2 of Examples.
Figure 12:
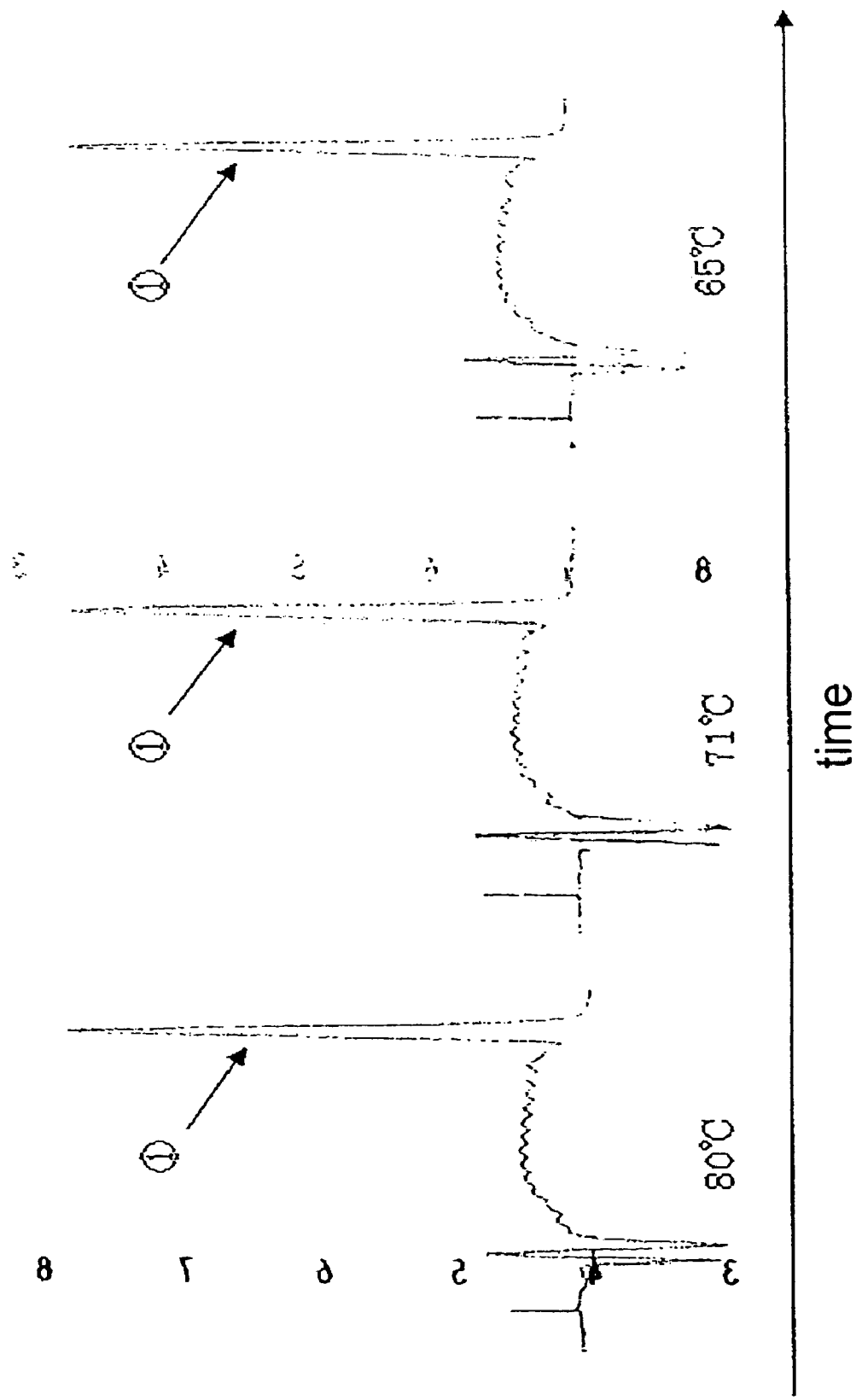
FIG. 12 is a chart representing the results of Experiment 2 of Examples.

1M HCl solution containing 2% hydrogen peroxide solution (65° C., 71° C., 80° C.) as a sample was deaerated using the deaerator A above and then was diluted at a ratio of 2:100 using ultrapure water as a pretreatment liquid N. Control information used is shown in Table 2. Also, a timing chart on the basis of this control information is shown in FIG. 11. In addition, conditions for measurement are shown in Table 3. The results are shown in Table 4 and FIG. 12.

TABLE 2

| | |
|---|---|
| 1)Z34 | transmit data for initialization (set the output position of the valve to the observer's right) and origin registration (at a rate of 30 Hz). |
| 2)Y34 | transmit data for initialization (set the output position of the valve to the observer's left) and origin registration (at a rate of 30 Hz). |
| A)R | perform the programs for the sample and diluent syringes. |
| 2)gV250IA24000M1000V5000AOM1000G3R<br>  a      b      c          b  d  e | sample syringe<br>a. move the valve to the input position at a rate of 250 Hz to sack 1 ml.<br>b. leave 1 second.<br>c. move the valve to the output position at a rate of 500 Hz to discharge 1 ml.<br>d. repeat a, b and c three times. (g . . . G3)<br>e. run |
| 1)V500IA21600 | diluent syringe<br>move the valve to the input position at a rate of 500 Hz to transmit data for sacking 9 ml. |
| 2)V250IA24000 | sample syringe<br>move the valve to the input position at a rate of 250 Hz to transmit data for sacking 1 ml. |
| A)R | perform the programs for the sample and diluent syringes. |
| 2)V5000A4320R | sample syringe<br>move the valve to the output position at a rate of 500 Hz to discharge up to a volume of 0.18 ml. |
| 1)V300AOR | diluent syringe<br>move the valve to the input position at a rate of 30 Hz to discharge the whole volume. |
| 1)V500IA21600R | diluent syringe<br>move the valve to the input position at a rate of 500 Hz to sack 9 ml. |
| 1)V300A0 | diluent syringe<br>move the valve to the output position at a rate of 30 Hz to transmit data for the whole volume discharge. |
| 2)V60A0 | sample syringe<br>move the valve to the output position at a rate of 6 Hz to transmit data for the whole volume discharge. |
| A)R | perform the programs for the sample and diluent syringes. |

TABLE 3

| | formulation of liquid chemical | flow velocity (μl/min) |
|---|---|---|
| B | 3M ammonium acetate | 500 |
| R | 0.16% DPD<br>0.2 mM citric acid | 50 |
| O | 10% hydrogen peroxide solution | 50 |
| C | 0.01 M HCl | 500 |
| S | 2% hydrogen peroxide solution<br>1M HCl (Fe and Cu 0.0 ppb) | — |

TABLE 4

| liquid temperature (° C.) | amount of included gas bubbles when sacking liquid sample (μl) | detection of gas bubbles by FIA measurement |
|---|---|---|
| 65 | 170 | not detected |
| 71 | 240 | not detected |
| 80 | 350 | not detected |

Illustration was made in BEST MODE and EXAMPLES herein on the premise of absorptiometry using a color developing reaction as a method for detection; however, the present invention is not limited thereto. For example, similar effects may be obtained using, as a method for detection, fluorometry, atomic absorption photometry, ICP spectrometry, ICP mass spectrometry and the like.

The invention claimed is:

1. A flow analysis system having a deaerator for removing gas bubbles in a liquid upstream an analysis section, wherein the deaerator comprises:

a liquid-containing means variable in internal volume for containing the liquid together with gas bubbles included in the liquid which is composed of a syringe and a plunger inserted in the syringe and movable in the axial direction of the syringe;

a switching means for switching between a liquid introducing path for introducing the liquid into the syringe and a liquid delivering path for delivering the liquid from the syringe;

a plunger driving means for moving the plunger between a liquid introducing direction for introducing the liquid into the syringe and a liquid delivering direction for delivering the liquid from the syringe; and a drive controlling means for controlling the switching means and the plunger driving means;

wherein, at the time of introducing the liquid into the syringe, the drive controlling means controls the plunger driving means to introduce the liquid into the syringe by moving the plunger along the liquid introducing direction, while the drive controlling means controls the switching means to keep setting to the liquid introducing path, and at the time of delivering the liquid from the syringe, after the drive controlling means controls the switching means to switch from the liquid introducing path to the liquid delivering path, the drive controlling means controls the plunger driving means to move the plunger along the liquid delivering direction to discharge gas bubbles in the syringe while maintaining in the syringe at least part of the liquid as a first step, and then to stop moving the plunger temporarily as a second step, and then to move the plunger further along the liquid delivering direction to deliver the liquid remaining in the syringe toward the analysis section as a third step.

2. The flow analysis system according to claim 1, which the drive controlling means controls the switching means and the plunger driving means in such a manner that the liquid introduction and the gas bubble discharge may be repeated until the liquid reaches a predetermined amount in the liquid-containing means.

3. The flow analysis system according to claim 1, wherein the syringe has an opening at its tip, the syringe being installed generally in the vertical direction with the opening facing upward.

4. The flow analysis system according to claim 3, wherein the opening functions as a liquid inlet for introducing the liquid into the liquid-containing means and/or as a liquid delivery port for delivering the liquid from the liquid-containing means to the analysis section and wherein the deaerator further comprises a switching means for switching in function between the gas bubble outlet and the liquid inlet and/or delivery port.

5. The flow analysis system according to claim 1, 2, 3 and 4, which is a flow injection analysis system.

* * * * *